US00PP29879P3

(12) United States Plant Patent
Stringer et al.

(10) Patent No.: US PP29,879 P3
(45) Date of Patent: Nov. 27, 2018

(54) BLUEBERRY PLANT NAMED 'GUMBO'

(50) Latin Name: *Vaccinium spp. Hybrid*
Varietal Denomination: Gumbo

(71) Applicant: The United States of America, as represented by the Secretary of Agriculture, Washington, DC (US)

(72) Inventors: Stephen J. Stringer, Picayune, MS (US); Arlen D. Draper, Payson, AZ (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/731,025

(22) Filed: Apr. 7, 2017

(65) Prior Publication Data

US 2018/0295760 P1 Oct. 11, 2018

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — John Fado; Ariel Atkinson

(57) ABSTRACT

The most distinctive features of the southern highbush blueberry 'Gumbo' are its early ripening, high yield, excellent fruit quality attributes, and excellent plant vigor under field and high density growth conditions.

2 Drawing Sheets

Latin name of genus and species of the plant claimed: 'Gumbo' is a new blueberry plant that is a *Vaccinium* spp. Hybrid.

Variety denomination: The new blueberry plant claimed is of the cultivar denomination 'Gumbo'.

BACKGROUND OF THE INVENTION

The present invention relates to a new and distinct hybrid of southern highbush blueberry (*Vaccinium* Sp. hybrid.) known as *Vaccinium* Sp. Hybrid. and herein referred to as 'Gumbo', as herein described and illustrated.

'Gumbo (Tested as MS 1377) originated from a cross of 'Cara's Choice' (Ehlenfeldt et al., 2005) X MS 6 made in 2000 in Poplarville, Miss. 'Cara's Choice' was derived from the cross of G 144 (northern highbush, NH) X US 165. US 165 is a complex species hybrid (southern highbush, SH) resulting from crosses among *V. corymbosum* selections and cultivars (both northern and southern highbush), *V. darrowii, V. constablaei*, and several *V. virgatum* (Rabbiteye, RE) selections and cultivars. MS 6 originated from a cross of F-72 (Wareham x Pioneer) x 'Berkeley' and 'Sharpeblue (NH and SH). Hence, the name 'Gumbo' was chosen to reflect the diverse combinations of both southern and northern blueberry species contributing to the genetic makeup of this new cultivar. 'Gumbo' was selected in 2003 by S. J. Stringer and A. D. Draper from the blueberry seedling nursery in Poplarville, Miss., and were subsequently propagated. 'Gumbo' was established in replicated field planting in Perkinston, Miss. in 2005 and McNeill, Miss., in 2009 along with other elite clones and cultivars and was subsequently evaluated by both S. J. Stringer and A. D. Draper. 'Gumbo' differs from its female parent 'Cara's Choice' in that its growth habit is more upright than that of 'Cara's Choice'. Additionally, it flowers approximately 8-10 days earlier and ripens about the same. Berries of 'Gumbo' have an average weight of over 2 grams which is a relative increase of approximately 20-25% over that of 'Cara's Choice', and measurements of berry firmness for 'Gumbo' are also greater than 'Cara's Choice' by a similar magnitude, 217 g/mm vs 159 g/mm (rate of force required to compress berries).

'Gumbo' has been asexually propagated on many occasions since 2003 by both hard wood and softwood cuttings at Poplarville, Miss. It roots readily from softwood cuttings and in all cases the clones propagated from cuttings have maintained the vegetative and fruit characteristics of the original selection.

'Gumbo' has been primarily compared with the current early southern highbush standard 'Star' (U.S. Plant Pat. No. 10,675) and 'Santa Fe' (U.S. Plant Pat. No. 10,788) grown under field conditions at Perkinston, Miss. over an 8 year period.

Over the eight year period of 2009 to 2016, the date of approximately 50% flowering of 'Gumbo' was an average of about 6 and 1 days later than 'Star' and 'Santa Fe', respectively while the average date of approximately 50% fruit ripening of 'Gumbo was about 8 and 5 days later, respectively, than these same cultivars. During the same time period, subjective comparisons were made annually on several plant and berry attributes using a scale of 1-10 with 10 being the most desirable; average ratings of cropping (productivity) for 'Gumbo' were 7.4, while those for 'Santa Fe' and 'Star' were 6.6 and 6.7, respectively. Plant vigor ratings were 8.1 for both 'Gumbo' and 'Santa Fe', and 7.5 for 'Star'. 'Gumbo' had an average berry color rating of 8.2 while both 'Santa Fe' and 'Star' had average berry color ratings of 7.8. Berry picking scar values were similar for all cultivars: 'Gumbo' and 'Santa Fe' were 8.0 and 'Star' was 7.9. Berry flavor was also similar for all cultivars: 8.0 for 'Gumbo', 7.9 for 'Santa Fe', and 7.8 for 'Star'. Laboratory evaluations provided empirical data comparing several fruit quality parameters. The average berry size of 'Gumbo' and 'Star' was approximately 2.1 grams while 'Santa Fe' was approximately 1.6 grams. pH values for 'Gumbo' berries averaged 3.11 while both 'Santa Fe' and 'Star' had an average pH of 3.3. Soluble solids content (Brix$^{0}$) for 'Gumbo', 'Star', and 'Santa Fe' were approximately 11.6, 12.5 and 12.5 respectively. Firmness values were 217.8 g/mm for 'Gumbo', 249.3 g/mm for 'Santa Fe' and 220.6 for 'Star' while % splitting of berries (percentage of split berries following 24 hour distilled water soaking) was 0.6 for 'Gumbo', 23.0 for 'Santa Fe', and 0.0 for 'Star'.

SUMMARY OF THE INVENTION

The following are the most outstanding and distinguishing characteristics of this new cultivar when grown under normal horticultural practices in Mississippi. 'Gumbo' is an early-mid season southern highbush blueberry having highly favorable fruit attributes, especially size, color, scar, and resistance to splitting. It is precocious, has excellent plant vigor, and is moderately-high yielding. It has chilling requirements similar to other early-mid season southern highbush cultivars, in the range of 350-400 hours.

DESCRIPTION OF THE PHOTOGRAPHS

Figure 1:
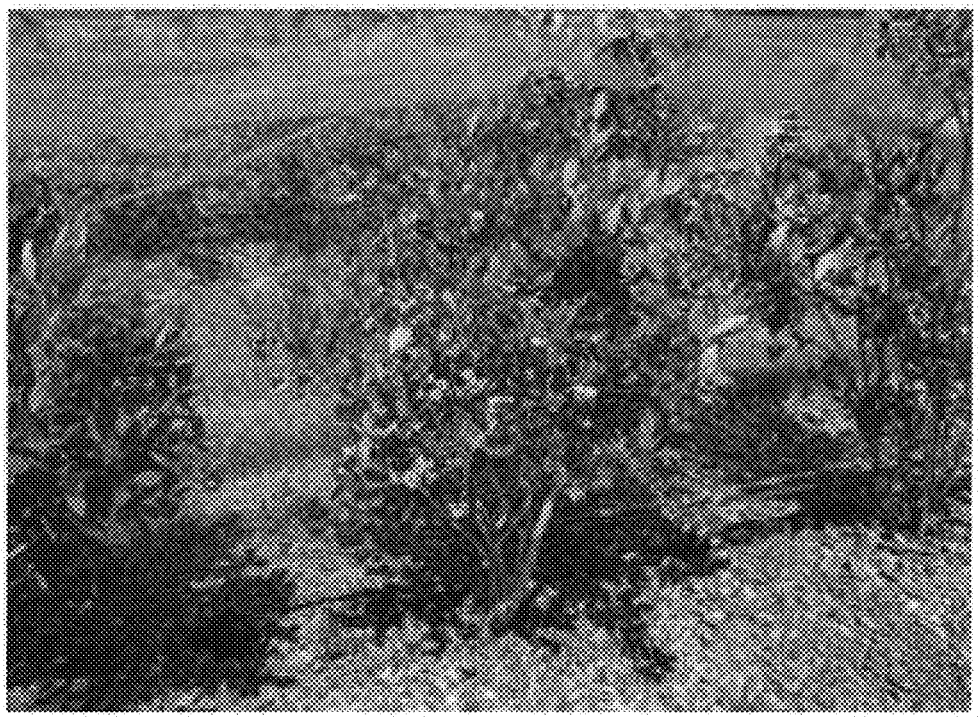
FIG. 1 shows a four year old 'Gumbo' plant and berries during ripening in May of 2014.
Figure 2:
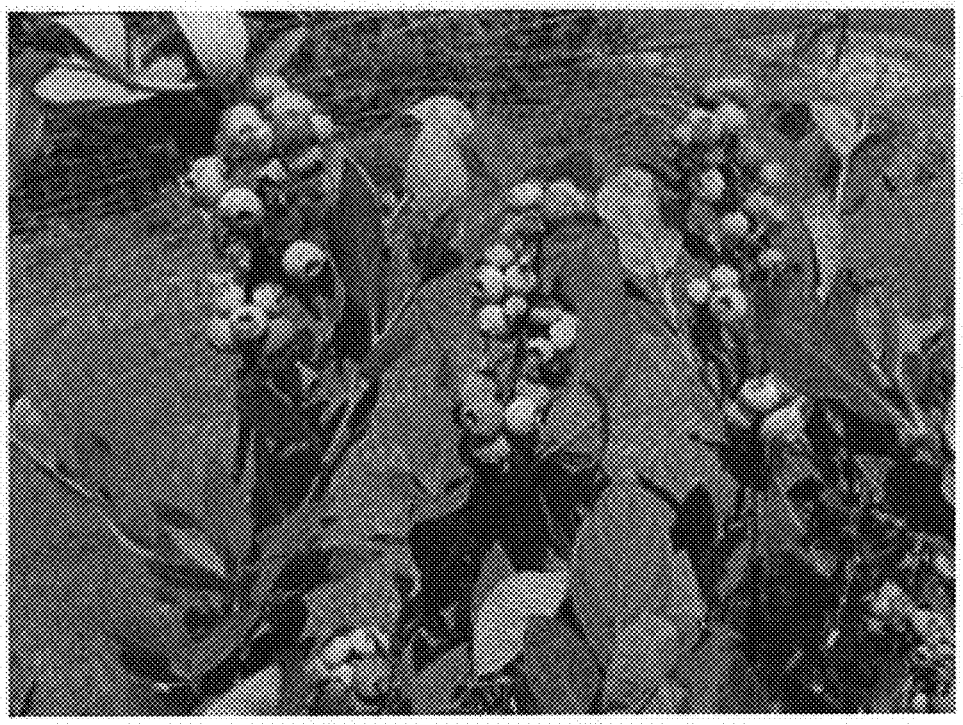
FIG. 2 shows ripening berry clusters in May of 2014.

The colors shown are as true as can be reasonably obtained by conventional photographic procedures.

DETAILED DESCRIPTION OF THE NEW CULTIVAR

The following is a detailed description of the botanical and pomological characteristics of the subject blueberry, 'Gumbo'. This description is in accordance with UPOV terminology. Color designations, color descriptions and other phenotypical descriptions may deviate from the stated values and descriptions depending upon variation in environmental, seasonal, climatic and cultural conditions. 'Gumbo' has not been observed under all possible environmental conditions. Color terminology follows The Royal Horticultural Society Colour Chart. London (R.H.S.) (4$^{th}$ edition, 2001), The descriptions reported herein are from four- to five-year-old specimens grown in McNeill, Miss. in soil amended with pine bark and with supplemental irrigation. The plants used for these observations were planted in 2011, and descriptive data were collected in 2015 and 2016.

PLANT

Size:

*Height*.—Approximately 1.4 to 1.8 m by about 4 years of age. Four year-old 'Gumbo' plants in South Mississippi reach a height of 1.3 to 1.6 m at the center of the plant.

*Width at the base or crown*.—Approximately 0.3 to 0.4 m.

*Width at the top of the bush*.—Approximately 0.9 to 1.1 m.

Growth habit: Moderately spreading with several canes arising from the crown.

Growth: Very high vigor. Grows moderately well in in heavy Coastal plains soils where many southern highbush blueberry cultivars die out after 3 years.

Productivity: Medium in plants gown in soils amended in soils with pine bark and supplemental irrigation.

Hardiness: Similar to other southern highbush cultivars like 'Star' and 'Santa Fe'.

Chilling requirements: Approximately 350-400 hours of temperature at or below 45° F. (about 7° C.) to induce normal leafing and flowering during the spring.

Leafing: Plants readily break numerous leaf buds simultaneously with flowering.

Canes: Canes 3 years old and older can be 11 to 18 mm in diameter. Color is Grey Brown 198B. 2 year old wood is 6 to eight mm in diameter, color is Yellow-Green 153D. Current season shoot is 2 to 3 mm in diameter, color is Yellow-Green 153D.

*Surface texture*.—Canes less than 3 years old are smooth. Canes 3-4 years old can become rough with some growth fissures and flaking bark. As canes become older, they become nearly smooth again.

Diseases: More tolerant to septoria leaf spot than 'Star' and 'Santa Fe'.

FOLIAGE

Leaf color: Healthy mature leaves.

*Top side*.—About Green 137A.

*Under side*.—About Yellow-Green 147C.

Leaf arrangement: Alternate, simple.

Leaf shape: Elliptic.

Leaf margins: Nearly entire, slightly crenate near base.

Leaf venation: Reticulate.

*Vein color*.—About yellow-green 153A.

Leaf apices: Acuminate.

Leaf bases: Acute to acuminate.

Leaf dimensions:

*Length*.—53 to 71 mm.

*Width*.—24 to 34 mm.

Leaf surface: Smooth with moderate wax.

Petioles: Small.

*Length*.—Approximately 3.0 to 4.5 mm.

*Color*.—About Yellow-Green 152D.

FLOWERS

Date of 50% anthesis: March 17 (8 year average in south MS). Blooming or flowering season for 'Gumbo' begins around March 3$^{rd}$ (10%) in south Mississippi, reaching 50% bloom on March 17$^{th}$ on average. Plants are 90% or more in bloom by March 27$^{th}$.

Flower shape: Urceolate.

Flower bud number: Medium to High.

Flowers per cluster: Approximately 5 to 8.

Flower fragrance: Yes. 'Gumbo' flowers have a slight rose to fruity fragrance if stored in an enclosed plastic bag for 15 minutes after harvesting the blossoms.

Corolla:

*Color*.—About White 155D open flower.

*Length*.—Approximately 8.5 to 9.5 mm.

*Width*.—Approximately 6.8 to 7.0 mm.

*Aperture width*.—Approximately 3.0 to 4.2 mm.

Flower peduncle:

*Length*.—Approximately 8 to 10 mm.

*Color*.—About Yellow-Green 145B.

Flower pedicle:

*Length*.—Approximately 3-4 mm.

*Color*.—About Yellow-Green 145B.

Calyx (with sepals):

*Diameter*.—5.0 to 5.5 mm; color Green 137B.

*Stamen*.—Length 6.5 to 7.0 mm; number per flower 10; color yellow-green 145 C.

*Style*.—Length 8.0 to 9.0 mm; color Yellow-Green 145A.

*Pistil*.—Length 11.0 to 12.0 mm; ovary color (exterior) Green 137D.

*Anther*.—Length 4.0 to 4.5 mm; number 10; color Greyed-Orange 167A.

*Pollen*.—Abundance — Medium; color Yellow-Orange 14D. The cultivar has a low to moderate degree of self-compatibility. It should be grown with another cultivar such as 'Star' (U.S. Plant Pat. No. 10,675) or 'Santa Fe' (U.S. Plant Pat. No. 10,788).

FRUIT

Date of 50% maturity: May 22 (year average in south MS). In south Mississippi, 'Gumbo' on average has 10% ripe berries on May 11th, 50% on May 22$^{nd}$, and 90% ripe berries by Jun 1$^{st}$.

Fruit development period: Fruit development period 60 to 65 days.

Berry color: With Wax Violet-Blue 97C; with wax removed greyed-Purple 187A to Black 202A.

Berry surface wax abundance: High.

Berry flesh color: Yellow-green 145C to Green-White 157A.

Berry weight: 1$^{st}$ harvest 2.1 to 2.5 g; 2$^{nd}$ harvest 1.6 to 2.2 g.

Berry shape: 'Gumbo' berry shape is nearly spherical.

Fruit stem scar: Small, dry, no tearing.

Berry firmness: Good.

Berry flower and texture: Mild flavor, excellent texture.

Storage quality: Good to very good.

Suitability for mechanical harvesting: Unknown, but berries are readily removed from pedicels by hand with gentle force.

Uses: Primarily used as fresh fruit for shipping.

Seed:

*Seed abundance in fruit*.—Low to medium.

*Seed color*.—Greyed-Orange 165B.

*Seed dry weight*.—48 mg per 100 seed.

*Seed size*.—Length 1.0 to 1.3 mm for fully developed seeds.

The invention claimed is:

1. A new and distinct cultivar of southern highbush blueberry plant, substantially as illustrated and described herein.

* * * * *